United States Patent [19]

Kirita et al.

[11] Patent Number: 4,559,034
[45] Date of Patent: Dec. 17, 1985

[54] LINE FOR USE IN BODY FLUID TREATMENT

[75] Inventors: Yasuzo Kirita, Toyonaka; Masaru Kawahashi, Takatsuki; Keiki Kariu; Kimihisa Sunahara, both of Saiki; Hidemune Naito, Kobe, all of Japan

[73] Assignees: Kawasumi Laboratories, Inc., Tokyo; Kuraray Co., Ltd., Kurashiki, both of Japan

[21] Appl. No.: 559,855

[22] Filed: Dec. 12, 1983

Related U.S. Application Data

[63] Continuation of Ser. No. 528,234, Aug. 30, 1983, abandoned, which is a continuation of Ser. No. 366,919, Apr. 9, 1982, abandoned.

[30] Foreign Application Priority Data

Apr. 16, 1981 [JP] Japan .............................. 56-55667[U]
Jul. 3, 1981 [JP] Japan .............................. 56-99643[U]

[51] Int. Cl.⁴ .............................................. A61M 1/03
[52] U.S. Cl. .......................................... 604/52; 604/5;
604/118; 210/321.3; 210/500.2
[58] Field of Search ......................................... 604/4-7,
604/52, 53, 118, 126, 252, 402, 122; 55/159;
210/500.2, 321.3; 128/DIG. 3, DIG. 13

[56] References Cited

U.S. PATENT DOCUMENTS

| 3,677,242 | 7/1972 | Shaye .................................... 604/126 |
| 3,841,157 | 10/1974 | Willock .............................. 604/4 X |
| 3,863,504 | 2/1975 | Borsanyi ..................... 128/DIG. 13 |
| 3,896,733 | 7/1975 | Rosenberg ............................... 604/4 |
| 3,929,741 | 12/1975 | Laskey .......................... 210/500.1 X |
| 3,986,956 | 10/1976 | Anno ....................................... 604/5 |
| 4,006,745 | 2/1977 | Sorenson et al. ....................... 604/4 |
| 4,033,345 | 7/1977 | Sorenson et al. ....................... 604/4 |
| 4,231,366 | 11/1980 | Schael ..................................... 604/4 |
| 4,248,736 | 2/1981 | Fuchigami et al. ..................... 604/4 |
| 4,303,068 | 12/1981 | Zelman .................................... 604/5 |
| 4,336,036 | 6/1982 | Leeke et al. .......................... 55/159 |

FOREIGN PATENT DOCUMENTS 50-683 1/1975 Japan .

OTHER PUBLICATIONS

Anno, Gousuki and Hidai, Hideo; "Transmembrane Pressure Stabilizer For Haemodialysis", *Biomedical Engineering*, Jan. 1976.

Naito, H., Miyazaki, T., Shimizu, N. and Yoneda, K., "Non-Anticoagulant Hemodialysis with Synthetic EVAL HFAK", Konan Hospital, Kobe, Japan.

Miyazaki, Tetuo et al., "Blood Line for Non-Anticoagulant Hemodialysis", 2/11/1982.

*Primary Examiner*—John D. Yasko
*Assistant Examiner*—Michelle Lester
*Attorney, Agent, or Firm*—Kramer and Brufsky

[57] ABSTRACT

A method for treating blood uses a tubular body fluid passageway member at least part of which is made of a flexible material, an outer tubular member which is made of a nonflexible material and contains said tubular body fluid passageway member hermetically enclosed therein, a pressure detecting member for monitoring the pressure of the flowing body fluid by means of a fluid filled in the hermetically closed space between the outside surface of said tubular body fluid passageway member and said outer tubular member without substantial contact of the body fluid with air, and a body fluid filtering member comprising a filter. The method is especially useful for non-anticoagulant hemodialysis.

7 Claims, 16 Drawing Figures

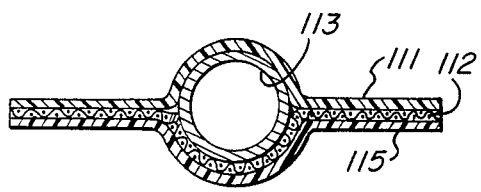
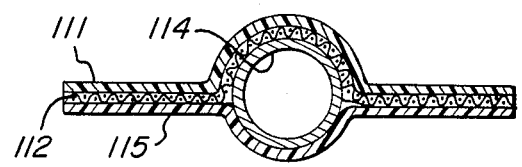
FIG. 9a  FIG. 9b
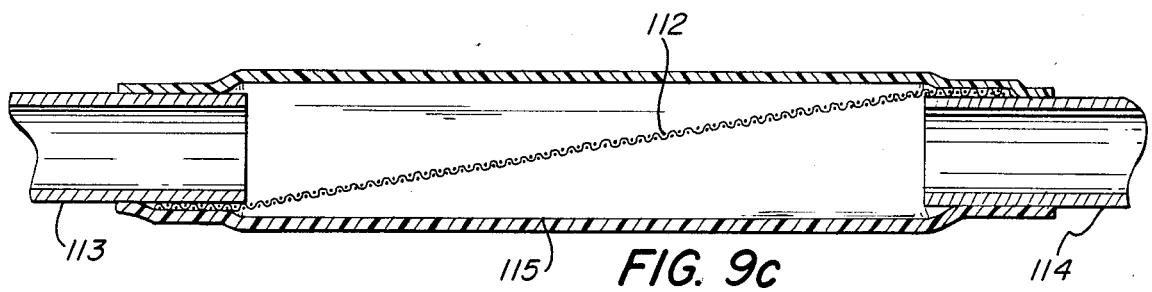
FIG. 9c
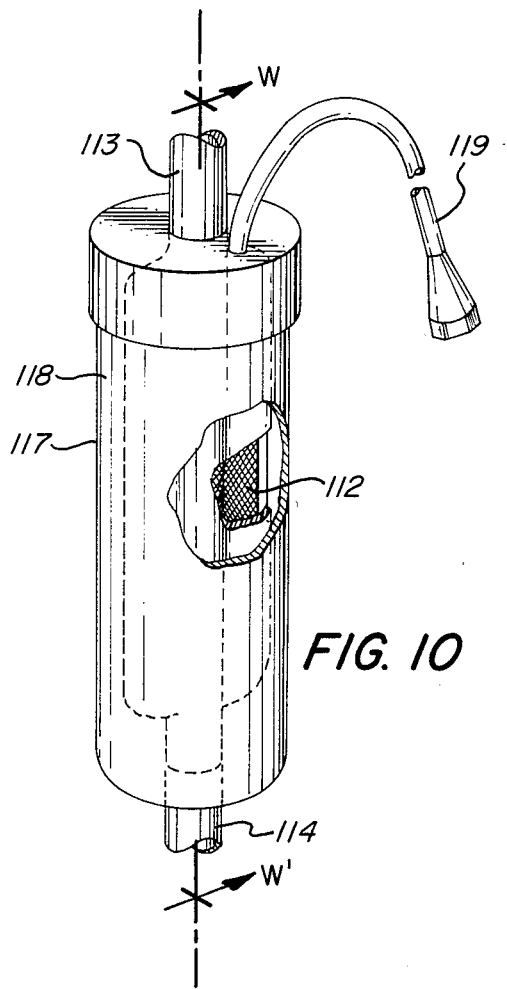
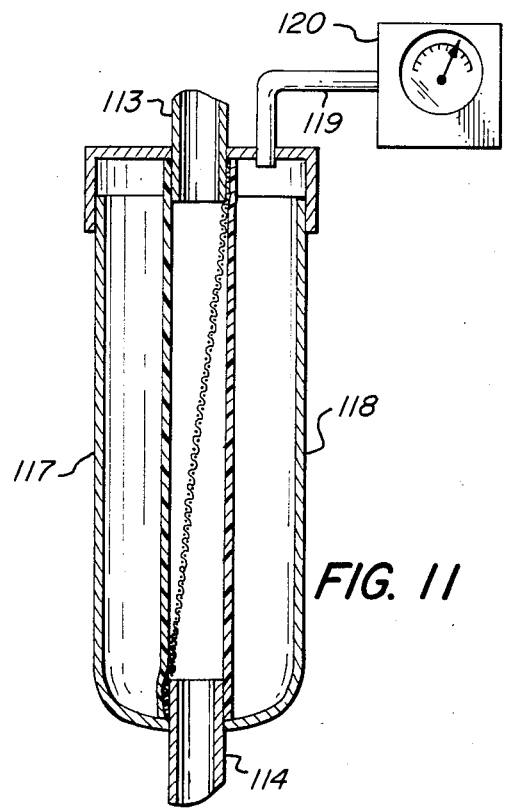
FIG. 10  FIG. 11

LINE FOR USE IN BODY FLUID TREATMENT

This application is a continuation of application Ser. No. 528,234, filed Aug. 30, 1983 which in turn is a continuation of application Ser. No. 366,919 filed Apr. 9, 1982, both now abandoned.

BACKGROUND OF THE INVENTION

1. Field of the Invention

This invention relates to a line for use in body fluid treatment using such a body fluid treating apparatus as an artificial kidney or an ascitic fluid treating apparatus, which line comprises a tubular member for connecting such apparatus to a patient and other necessary constituent members of the treating system.

2. Description of the Prior Art

In operating an apparatus for the extracorporeal treatment of a body fluid, such as blood or ascitic fluid, a line device for leading the body fluid to the apparatus and then back to the body is generally used. The line device comprises a tubular member, which serves as the passageway for the body fluid, and as necessary a pressure monitor means, a pressure adjustment means, a bubble removing means, a filter means, a sampling or drug addition means, etc. Among these means, the conventional pressure monitor means (cf. FIG. 1) is connected with a drip chamber, which serves as a bubble removing means, and the pressure gauge is actuated by means of the air within an air reservoir disposed in the line. In the conventional body fluid treatment, heparin is added to the body fluid to prevent the fluid from coagulation (in case of the blood, from clotting) or urokinase is added to dissolve coagulates or clots, so that the provision of an air reservoir or chamber in the line does not produce any problems.

However, it is recently pointed out that the use of the above-mentioned anticoagulant and other agents causes and increase in physiological load on the patients' side and an increase in bleeding tendency in patients (e.g. in post-operative dialysis or dialysis in females in the menstrual phase). Thus it is said that reduction in quantity or nonuse of such anticoagulant or the like is desirable. When a body fluid is treated with a reduced quantity of an anticoagulant or without use thereof (hereinafter collectively referred to as "reduction in quantity"), the provision of a space in which air is present, such as an air reservoir, in the line must be avoided strictly, since body fluids are easy to coagulate upon exposure to air. Accordingly, it has become necessary to provide a pressure detecting means which avoids contact of body fluids with air and can be used as a substitute for the conventional air-actuated pressure detecting means in the conventional line.

SUMMARY OF THE INVENTION

The present invention solves such problem. Thus, the invention provides a line for use in body fluid treatment which comprises a tubular body fluid passageway member at least part of which is made of a flexible material, an outer tubular member which is made of a nonflexible material and contains said tubular body fluid passageway member hermetically enclosed therein, a pressure detecting member for monitoring the pressure of the flowing body fluid by means of a fluid filled in the hermetically closed space between the outside surface of said tubular body fluid passageway member and said other tubular member without substantial contact of the body fluid with air, and a body fluid filtering member comprising a filter, the body fluid passing the filter from the inside to the outside.

In another aspect, the invention provides a line for use in body fluid treatment which comprises a tubular body fluid passageway member which is at least partly made of a flexible material and is integrated with a built-in filter, an outer tubular member which is made of a nonflexible material and contains said tubular body fluid passageway member hermetically enclosed therein, and a pressure detecting member for monitoring the pressure of the flowing body fluid by means of a fluid filled in the hermetically closed space between the outside surface of said tubular body fluid passageway member and said outer tubular member without substantial contact of the body fluid with air.

BRIEF DESCRIPTION OF THE DRAWINGS

In the accompanying drawings,

FIG. 9 shows sectional views of the member illustrated in FIG. 8 as taken along lines X-X' [sectional view (a)], Y-Y' [sectional view (b)] and Z-Z' [sectional view (c)], respectively;

FIG. 10 shows a further embodiment of the line for body fluid treatment in accordance with the invention;

FIG. 11 shows a sectional view taken along the line W-W' in FIG. 10;

DETAILED DESCRIPTION OF THE INVENTION

Figure 1:
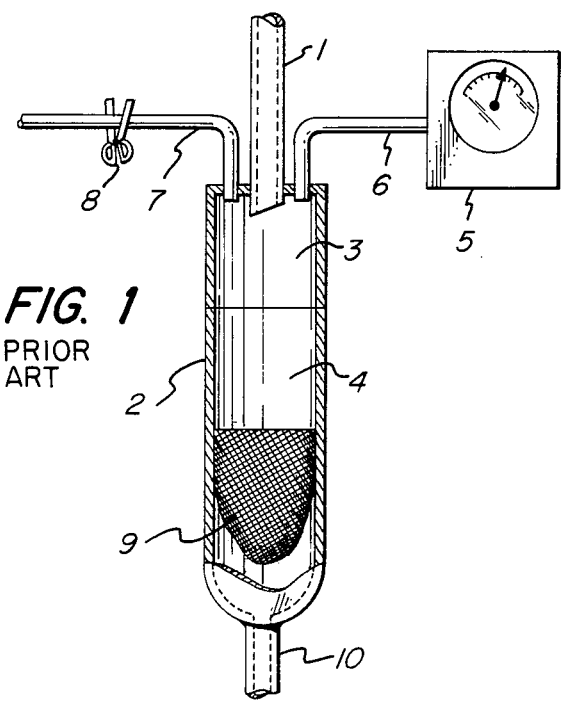
FIG. 1 shows a conventional line for body fluid treatment.

In FIG. 1, there are shown the pressure detecting means and filtering means to be used in a conventional line for body fluid treatment. The tubular body 1 is connected with the outer tube 2. In the upper part of the outer tube, there is formed an air reservoir 3. The body fluid stays in the lower part of the tubular body, as shown by 4. This device is generally called a drip chamber or air trap (hereinafter "drip chamber"), and the outer tube 2 performs the function of removing bubbles which form in the body fluid. In other words, while the body fluid remains in the outer tube 2, the bubbles rise to the upper part of the tube, so that the bubbles are separated and the body fluid becomes bubble-free. This outer tube 2 is fitted with a tubing 6 which connects the air reservoir 3 to a pressure gauge 5, so that the pressure of the body fluid can be known by detecting the pressure of the air retained in the air reservoir 3 by means of the pressure gauge. The air reservoir 3 is further fitted with a tubing 7 for liquid level adjustment. The tubing 7 for such adjustment is used to maintain the liquid level at an adequate level in such a manner that, when the quantity of air in the air reservoir becomes excessive, the forceps or clamp 8 is opened and the air is released from the system by means of a syringe or the like, or that, when the quantity of air becomes so small as to allow the back flow of the body fluid into tubings 6 and 7, the forceps or clamp 8 is opened in like manner and air is introduced from the external system by means of a syringe or the like. In the conventional line for body fluid treatment, the pressure detecting means is formed, as mentioned above, by making the best use of the mechanism of the drip chamber which removes bubbles in the body fluid. Furthermore, a filter 9, such as a bag-like mesh body, is provided in the lower part of the outer tube 2. The body fluid flows from the inside of the bag-like mesh body to the outside thereof. Said mesh body prevents coagulates, which possibly form in the above-mentioned drip chamber, the dialyzer etc., from returning to the patient's body by filtering off said coagulates. The body fluid which has permeated the body fluid filtering member comprising the mesh body is taken out through another tubular body 10.

In the conventional line for body fluid treatment, as mentioned above, the body fluid comes into contact with air while air is utilized in the pressure detecting means. Therefore, when treated in said line, the body fluid containing a reduced quantity of an anticoagulant or the like can easily give coagulates or clots, which are severely hazardous to the patient. There is also possibility of contamination with adventitious microorganisms from air. Direct contact of air and the body fluid is thus undesirable.

Figure 2:
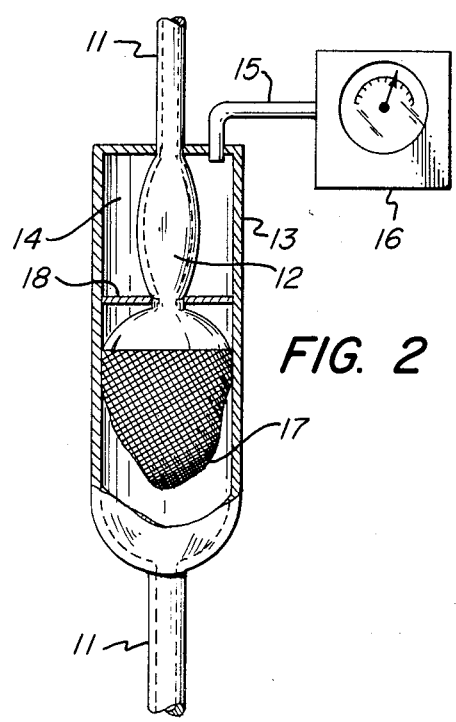
FIG. 2 shows an embodiment of the line for body fluid treatment in accordance with the invention.
Figure 3:
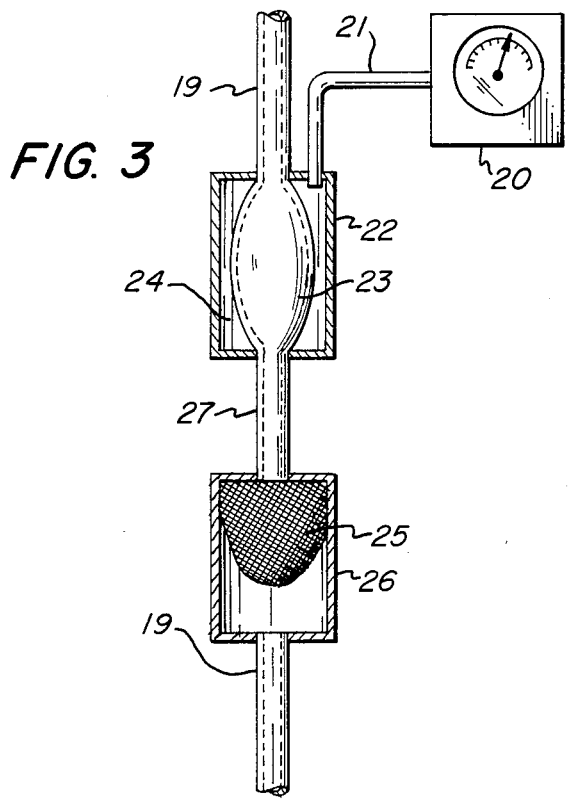
FIG. 3 shows another embodiment of the line for body fluid treatment in accordance with the invention.

In FIG. 2 and FIG. 3, there are shown two examples of the line for body fluid treatment in accordance with the present invention. In FIG. 2, a tubular body 11 for introduction of a body fluid is connected with a body fluid passageway tube 12 at least partly made of a flexible material. Said body fluid passageway tube 12 is hermetically contained in an outer tube 13 made of a nonflexible material. The phrase "hermetically contained" means not only that any fluid leakage does not occur between the body fluid passageway tube and the outer tube but also that there is no unnecessary outflow of a fluid from the outer tube 13 into the environment. The hermetically closed chamber 14 between the outside surface of the body fluid passageway tube and the outer tube is filled with a compressible or incompressible fluid such as air, physiological saline or glucose solution. Said hermetically closed chamber 14 is fitted with a tubing 15 which is communicated with a pressure gauge 16. The body fluid flowing through the body fluid passageway tube 12 causes inflation or deflation of the body fluid passageway tube depending on the pressure of said body fluid. A volume change due to the inflation or deflation causes a corresponding change in the pressure of the fluid in the hermetically closed chamber 14, and changes in the fluid pressure within said hermetically closed chamber 14 can be detected accordingly. In this case, the fluid used in the pressure detecting means and the body fluid never come into direct contact with each other. Even when air is used as the former fluid, the body fluid does not come into contact with the air. The pressure gauge 16 may be of any type but preferably is a pressure transducer which is capable of converting a pressure to an electric power. For precision of the pressure transfer, the tubing 15 should preferably be as short as possible. It is necessary that the tubing 15 has a sufficient thickness to prevent the expansion of it when the pressure is increased. Since there is possibility that an accidental leakage should occur in the body fluid passageway tube, physiological saline or glucose solution is preferred as the fluid in the hermetically closed chamber to air from the safety viewpoint. Such solution is preferable also for the reason that a liquid is an incompressible fluid and therefore superior as the means for pressure transfer. The flexible material for the body fluid passageway tube 12 may be any material having a flexibility sufficient to respond to the pressure of the body fluid flowing through the tube and includes, among others, silicones, polyurethanes, plasticized polyvinyl chloride, natural and synthetic rubbers. They have a sufficient flexibility when they have a thickness of 0.1 to 1 mm, preferably 0.2 to 0.5 mm. The nonflexible material for the outer tube 13 may be any material having a rigidity sufficient to prevent the material from absorbing any pressure change in the fluid within the hermetically closed chamber and includes, among others, polypropylene, polyethylene, rigid polyvinyl chloride, polycarbonates, other plastics, and metals.

Since the body fluid passageway tube in the line of the invention is made of a flexible material and the inflation or deflation of said flexible material is utilized in the pressure detection, said tube should preferably be used in the range within which the flowing body fluid exerts a positive pressure or a slightly negative pressure. When the flowing body fluid exerts a highly negative pressure, the flexible material portion shows a greater degree of deformation, which may undesirably lead to closure of the passageway. The line of the invention is thus especially useful as a line for body fluid treatment which is to be operated within the pressure range from a positive pressure to a slightly negative pressure.

Figure 4:
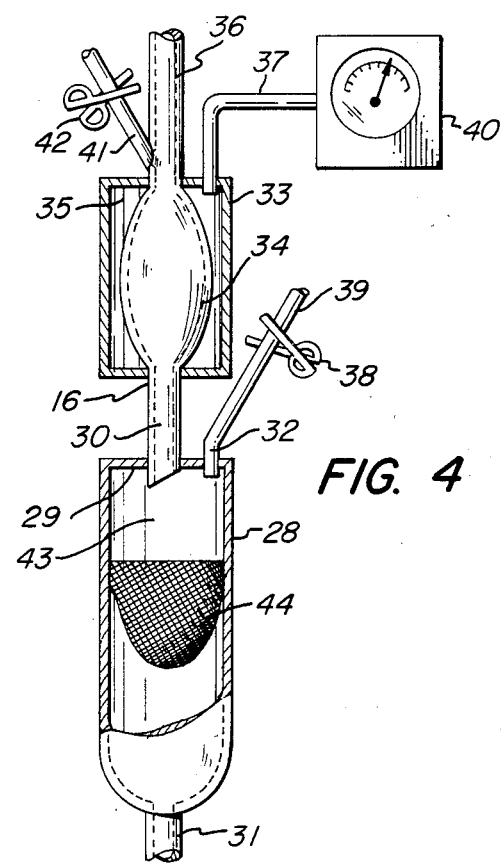
FIG. 4 shows a further embodiment of the line for body fluid treatment in accordance with the invention.

A filtering member comprising a filter 17 such as a bag-like mesh body is disposed before or after the above-mentioned pressure detecting means. In FIG. 2, the hermetically closed chamber 14 and the portion containing the mesh body 17 are separated from each other by a partitioning wall 18. The partitioning wall 18 preferably has a shape or structure such that the body fluid does not remain long or make a turbulent flow. The filtering means may be disposed either adjacent to the pressure detecting means or, as shown in FIG. 3, apart therefrom via a tubular body 27. The order of disposition of the pressure detecting means and filtering means is optional. However, in view of the possibility of coagulate formation, it is preferable that the filtering means is closer to the patient, since, in that case, the coagulates are not returned to the patient. In any case, the line for body fluid treatment is required to be provided with a filtering means comprising a filter such as a mesh body. Since FIG. 2 and FIG. 3 are common in many points, no particular explanation is made referring to FIG. 3, in which 19 is a tubular body, 20 a pressure gauge, 21 a tubing, 22 an outer tube, 23 a body fluid passageway tube, 24 a hermetically closed chamber, 25 a mesh body, 26 an outer tube and 27 a tubular body. In the figure, the body fluid such as blood flows in the direction from the top to the bottom of the drawing. Since FIG. 4 and FIG. 2 are common in many points, no particular explanation is made referring to FIG. 4, in which 28 is an outer tube, 29 the top of the outer tube 28, 30 a tubular body, 31 a tubular body, 32 an air drain tube, 33 an outer tube, 34 a body fluid passageway tube, 35 a hermetically closed chamber, 36 a tubular body, 37 a tubing, 38 a clamp, 39 the outlet for the air drain, 40 a pressure gauge, 41 an air drain tube, 42 a clamp, 43 the inside of the outer tube 28, and 44 a mesh body.

Figure 5:
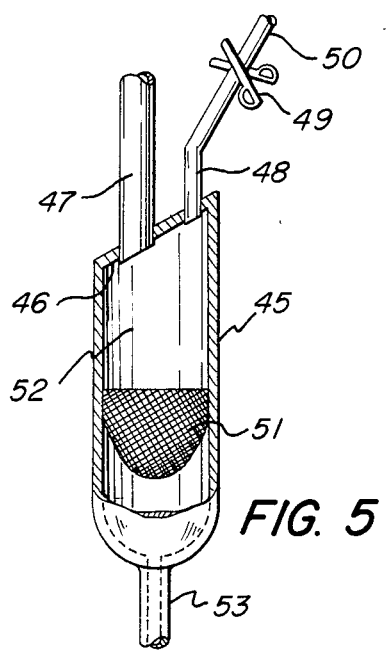
FIG. 5 shows an embodiment of the filtering member as intended for use in the line of the invention, said embodiment comprising a built-in filter.
Figure 6:
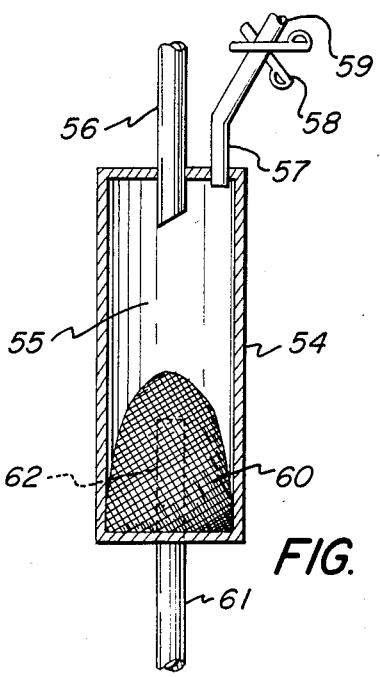
FIG. 6 shows another embodiment of the filtering member.

FIG. 5 and FIG. 6 each shows a filtering means which contains a built-in filter and is to be used in practicing the invention. In FIG. 5, 45 is an outer tube, 46 is the top of the outer tube 45, 47 a tubular body, 48 an air drain tube, 49 a clamp, 50 the outlet for the air drain, 51 a mesh body, 52 the inside of the outer tube 45, and 53 a tubular body. When the top of the outer tube 46 is slanted, as shown in FIG. 5, the air present in the body fluid can easily be taken out through the air drain tube 48. In FIG. 6, 54 is an outer tube, 55 the inside of the outer tube 54, 56 a tubular body, 57 an air drain tube, 58 a clamp, 59 the outlet for the air drain, 60 a mesh body, 61 a tubular body, and 62 a tubular body protruding into the outer tube 54. In FIG. 5 and FIG. 6, the body fluid such as blood flows in the direction from the top to the bottom of the drawing.

Figure 7:
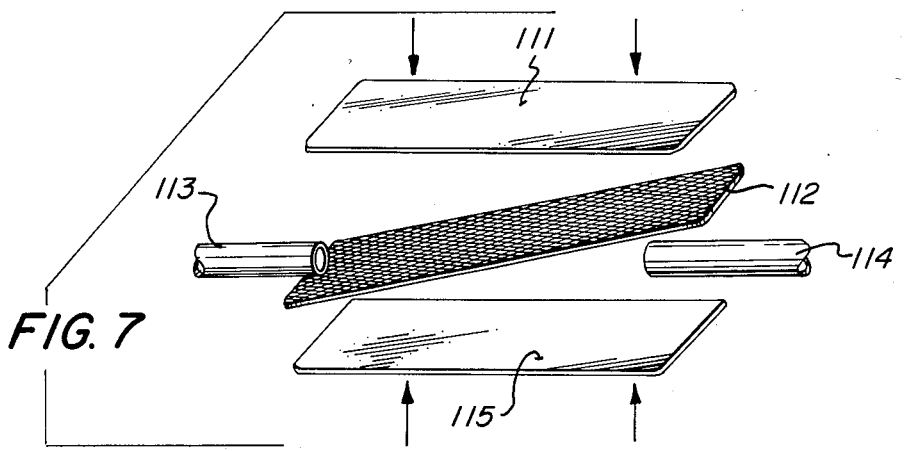
FIG. 7 is an assembly diagram for a body fluid passageway member to be used in the line of the invention.
Figure 8:
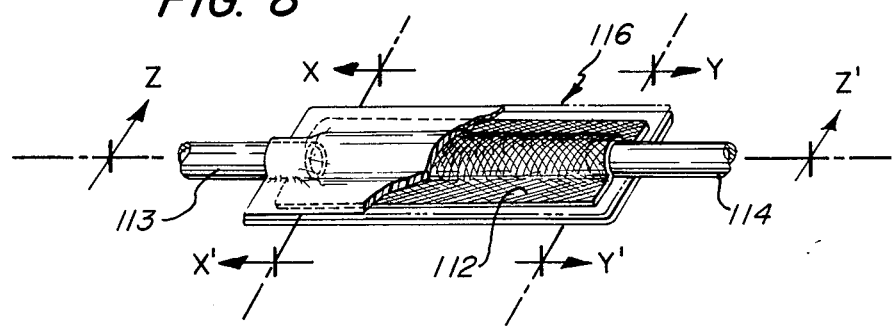
FIG. 8 shows the body fluid passageway member illustrated in FIG. 7 when the assemblage is complete.
Figure 12:
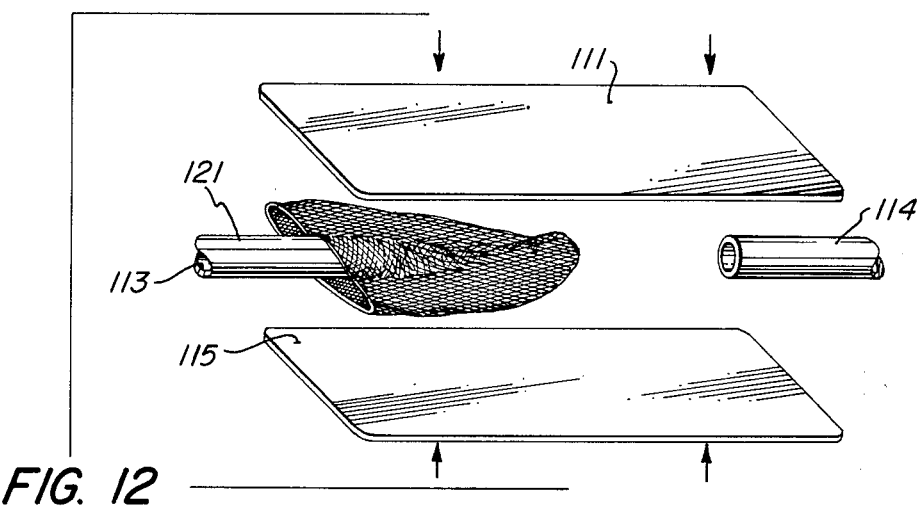
FIG. 12 is an assembly diagram for a body fluid passageway member to be used in the line of the invention.
Figure 13:
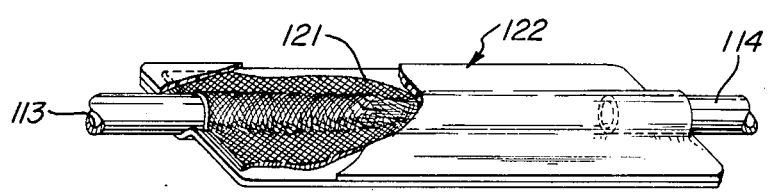
FIG. 13 shows the member illustrated in FIG. 12 when the assemblage is complete.

FIGS. 7, 8, 9, 10 and 11 illustrate a further embodiment of the invention, and FIGS. 11 and 12 a still further embodiment. A filter 112 is inserted between two flexible sheets 111 and 115 (FIG. 7). A body fluid inlet tube 113 and a body fluid outlet tube 114 are positioned on the sheet 111 at the opposite shorter sides in such a manner that the inlet and outlet are positioned on the different sides with respect to the filter 112. The sheets and filter are superposed as shown, and tightly sealed together on the circumference by simultaneous welding or adhesion or some other technique, so that a body fluid passageway tube 116 as shown in FIG. 8 is constructed, which tube has openings only at the body fluid inlet and outlet. The body fluid passageway tube 116 is hermetically housed in an outer tube 117 made of a nonflexible material as shown in FIG. 10. The phrase "hermetically housed" means that no fluid leakage can occur from between the body fluid passageway tube and the outer tube and that no unnecessary fluid outflow can take place from the outer tube 117 to the environment. The hermetically closed chamber 118 between the outside surface of the body fluid passageway tube and the outer tube is filled with a compressible or incompressible fluid such as air, physiological saline, or glucose solution. The closed chamber 118 is fitted with a tubing 119 communicating with a pressure gauge 120 shown in FIG. 11. FIG. 11 shows a sectional view, taken along the line W-W' (FIG. 10), of the pressure detecting means according to the invention as shown in FIG. 10. FIG. 11 further illustrates the state in which the pressure detecting means is connected to the pressure gauge 120 by means of the tubing 119. The body fluid flowing through the body fluid passageway tube causes inflation or deflation of the body fluid passageway tube depending on the pressure of the body fluid. A change in the volume of said tube causes a corresponding change in the fluid pressure in the hermetically closed chamber 118 and the change in the fluid pressure within said closed chamber 118 can be monitored. Therefore, the fluid in the pressure detecting means and the body fluid do not come into direct contact with each other. Even when air is used as the fluid, the body fluid does not come into contact with the air.

Furthermore, in accordance with the above embodiment, the filter 112 is disposed within the body fluid passageway tube 116. The filter is used for preventing any coagulates, if formed during the body fluid treatment, from returning to the patient. In integrating the built-in type filter with the body fluid passageway tube, the filter 112 or 121 is inserted between two sheets having an adequate size and made of a flexible material such as polyvinyl chloride, as shown in FIG. 7 or FIG. 12. The body fluid inlet tube 113 and the body fluid outlet tube 114 are positioned on the opposite ends of each sheet so as to allow the body fluid to pass through the filter. The sheets and the filter superposed as shown are tightly sealed together on the circumference by simultaneous welding or adhesion or some other technique. For tighter sealing, the body fluid inlet and outlet tubes are preferably made of a material adherent to or compatible with the sheets. The filter is preferably a mesh-like one or the like which is less resistant against the fluid flow.

When the body fluid passageway tube is constructed in this manner, said tube can be manufactured simply and efficiently from the productivity standpoint. Thus, in accordance with the embodiment, the tube can be produced at a lower cost without any need of disposing a separate filtering means for the same purpose. Moreover, since the filtering means and the body fluid passageway tube are integrated to one body, body fluid filtration and pressure detection can be conducted with a miniaturized line. The principal object is of course to provide a pressure detecting means which prevents the body fluid from direct exposure to air, as compared with the conventional pressure detecting means, and thereby contributes to the prevention of body fluid coagulation during extracorporeal circulation.

The surface of the filter, such as a mesh body, to be used in the practice of the invention is preferably made of a bubble-repelling material. When such a measure is taken, the mesh body surface can remain bubble-free, hence blood coagulation or clot formation need not be feared, and the line can be used safely without causing blood coagulation even when the body fluid is treated in the presence of a reduced amount of an anticoagulant.

As the bubble-repelling material for making or coating the filter mesh body, a hydrophilic polymer disclosed in Japanese Patent Application Laid-open No. 683/1975 and having an angle of receding contact with water of not more than 45° can preferably be used. The polymer should preferably have a good biocompatibility. Examples of such polymer are polymers of hydroxyethyl methacrylate, hydroxypropyl methacrylate, methoxyethyl acrylate, ethoxyethyl acrylate, diacetone acrylamide and vinyl alcohol. Copolymers of the above-mentioned monomers, hydroxyethyl acrylate, hydroxypropyl acrylate, diethylene glycol (meth)acrylate, dimethylaminoethyl (meth)acrylate (and quaternary ammonium salts thereof), 2-hydroxy-3-(meth)acryloylpropyldimethylamine (and quaternary ammonium salts thereof), (meth)acrylic acid, (meth)acrylamide, methyl(meth)acrylamide, ethyl(meth)acrylamide, propyl(meth)acrylamide, dimethyl(meth)acrylamide, vinylpyridine, vinylpyrrolidone and the like with other hydrophobic monomers, such as olefin, may also be used.

The filtering mesh body is advantageously prepared by coating a conventional filtering mesh body with any of these polymers. However, it is also possible to make the filtering mesh body itself using any of said polymers as the starting material. The most preferable hydrophilic polymers for use in coating the filtering mesh body includes polymers prepared from hydroxyethyl acrylate, hydroxypropyl acrylate, vinylpyrrolidone or an acrylamide. Polymers prepared from quaternary ammonium salt group-containing monomers or from monomers easily convertible to quaternary ammonium salts can also be used efficiently in many cases. They have an advantage that heparin can be immobilized thereon.

In case a coating having a receding contact angle for water of not more than 45° is formed by the graft polymerization method, almost all water-soluble monomers can be used with advantage. The receding contact angle for water as referred to herein is the one measured at 25° C.

The coating of the surface of the filtering mesh body with a hydrophilic polymer having a receding contact angle for water of not more than 45° can be conducted, for example, by the graft polymerization method or the coating method. The graft polymerization method comprises causing active points, such as radicals, to form on the surface of the filtering mesh body by the use of gamma ray, electron ray or ozone, for instance, and allowing a hydrophilic polymer-forming monomer or monomers to come into contact with the active points, whereby the polymerization takes place and a coating is formed. The active point formation is carried out in the presence or absence of said monomer or monomers. The coating method comprises preliminarily synthesizing a hydrophilic polymer, applying a solution or latex of the polymer to the surface of the filtering mesh body and allowing the solvent to evaporate so as to give a hydrophilic polymer coating. For improving the adhesiveness in carrying out the solution coating method, it is preferable in some cases to preliminarily treat the surface of the filtering mesh body with chromic acid-sulfuric acid, sodiumnaphthalene, ultraviolet rays, etc. Although the abovementioned solution method is most preferable from the workabability standpoint, the grafting method is preferred when the properties of the coating obtainable are taken into consideration. Since even a very thin coat formed on the surface of the filtering mesh body can improve the filtering mesh body with regard to the bubble repellency and compatibility with living cells, the thickness of the coat is preferably not more than 0.1 mm with due regard to mechanical properties. Especially suited is a thickness in the order of 10 millimicrons. For stability of such a thin coat layer, the hydrophilic polymer to be used in the coating method is required to be water-insoluble and have a molecular weight of not less than 10,000, preferably not less than 30,000.

Figure 14:
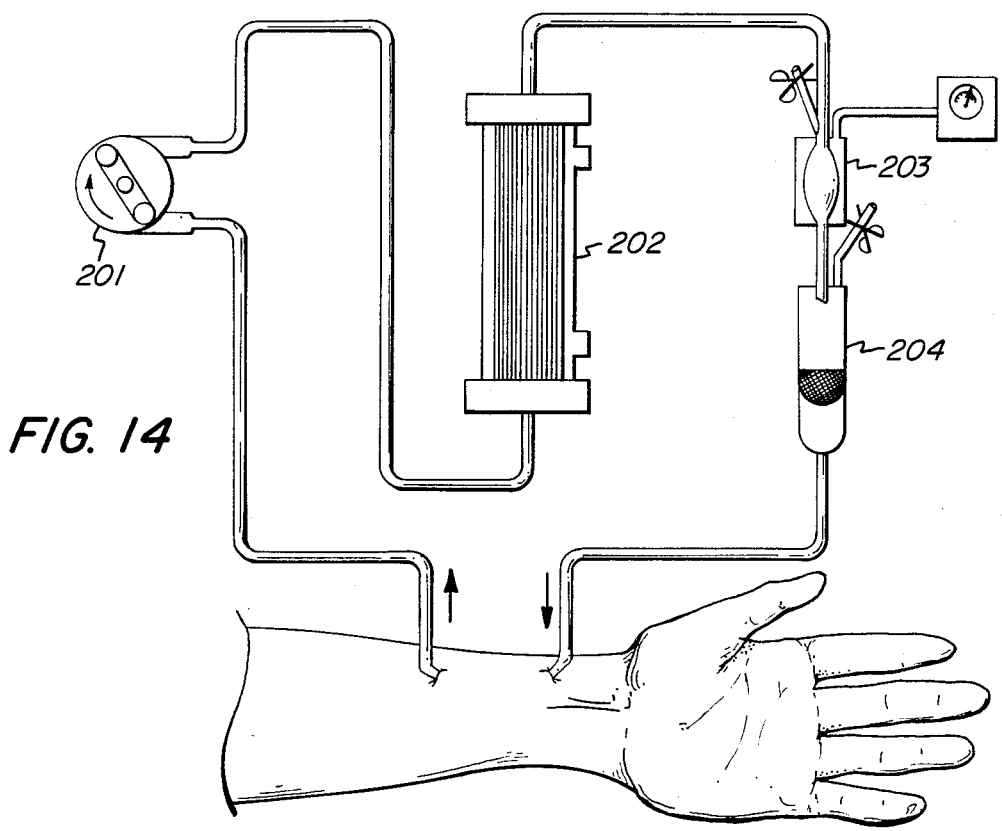
FIG. 14 is the block diagram of a non-anticoagulant hemodialysis system in which the line for body fluid treatment shown in FIG. 4 is used.

FIG. 14 shows a block diagram illustrating a hemodialysis system using a line for body fluid treatment according to the invention as shown in FIG. 4. The system is suited for performing hemodialysis without using any anticoagulant such as heparin. Said line comprises the pressure monitor chamber 203 and filter/degasser chamber 204 shown in FIG. 14. 201 is a blood pump. Using the system shown and, as the dialyzer 202, a module containing ethylene-vinyl alcohol copolymer hollow fiber ("KF 101"; Kuraray Co., Ltd.) bundles, hemodialysis was carried out without using any anticoagulant such as heparin during dialysis. The dialyzer was pretreated with 1,000 ml of physiological saline containing 400 mg of gabexate mesylate (G.M.). The dialysis conditions were as follows:

| | |
|---|---|
| Blood flow rate | 200 ml/min. |
| Blood pressure before entrance into the dialyzer, $P_{Bin}$ | 20 mmHg |
| Blood pressure after leaving from the dialyzer, $P_{Bo}$ | 50 mmHg |
| Dialysate flow rate | 500 ml/min. |
| Dialysis pressure | To be maintained at $-200$ mmHg by means of a vacuum pump. |
| Transmembrane pressure | 260 mmHg |
| Pressure monitor chamber: | Outer tube: Rigid polyvinyl chloride |
| | Blood passageway tube: Plasticized polyvinyl chloride, 0.4 mm thick |
| | Fluid in hermetically closed chamber: Air |
| Filter/degasser chamber | Mesh body: Mesh body made of a polyester and coated with a poly(hydroxyethyl methacrylate) resin |

During the dialysis, the blood substantially did not come into contact with air in the pressure monitor chamber 203 or in the filter/degasser chamber 204, and consequently any troubles such as blood coagulation were not encountered. Any troubles including blood coagulation were not encountered in any other circuit lines including the dialyzer, either. The pressure monitor chamber 203 functioned in a satisfactory manner, detecting the $P_{Bo}$ precisely.

The term "non-anticoagulant hemodialysis" as used herein means hemodialysis performed without using any anticoagulant, such as heparin, during dialysis.

In an extracorporeal circulation system such as an artificial kidney or ascitic fluid treating system, reduction in the anticoagulant use level cannot be achieved without an adequate line even if the treatment device (for example, a hemodialyzer using an ethylene-vinyl alcohol copolymer hollow fiber membrane) itself can well prevent the body fluid from coagulation. The line for body fluid treatment in accordance with the present invention, which line is designed for the prevention of body fluid coagulation, has made it possible for the first time to perform non-anticoagulant body fluid treatment successfully. The effect of the present invention is thus very great.

What is claimed is:

1. A method for the extracorporeal treatment of blood comprising the steps of:
   providing a circuit without a drip chamber for carrying blood to which substantially no anticoagulant has been added from a patient and returning the blood to the patient without substantial contact of the blood with air;
   dialyzing blood within said circuit with an ethylenevinyl alcohol copolymer hollow fiber dialyzer;
   passing the blood within said circuit through a tubular blood passageway member in series with said dialyzer, at least part of which is made of a flexible material;
   hermetically enclosing the tubular blood passageway member within an outer tubular member made of a nonflexible material;
   filling the hermetically closed space between the outside surface of said tubular blood passageway member and said outer tubular member with a fluid; and detecting changes in the pressure of said fluid caused by inflations and deflations of the flexible portion of the tubular blood passageway produced by changes in the pressure of the blood passing therethrough.

2. The method of claim 1 including the additional step of filtering the blood.

3. The method of claim 2 wherein the filtering is done with a filter having a filter surface made of a bubble-repelling material.

4. The method of claim 3 wherein the bubble-repelling material is a hydrophilic polymer, the angle of receding contact of water with said polymer being not more than 45°.

5. The method of claim 2 wherein the filtering is done with a built-in filter integrated with the tubular body fluid passageway.

6. The method of claim 3 wherein the filtering is done with a built-in filter integrated with the tubular blood passageway.

7. The method of claim 4 wherein the filtering is done with a built-in filter integrated with the tubular body fluid passageway.

* * * * *